US00PP37666P3

(12) United States Plant Patent
Ammerlaan

(10) Patent No.: US PP37,666 P3
(45) Date of Patent: Sep. 1, 2026

(54) ***ARISTALOE* PLANT NAMED 'OVROCKS16'**

(50) Latin Name: *Aristaloe aristata*
Varietal Denomination: OVROCKS16

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 58 days.

(21) Appl. No.: 18/831,537

(22) Filed: Apr. 4, 2025

(65) Prior Publication Data

US 2026/0150769 P1 May 28, 2026

(30) Foreign Application Priority Data

Nov. 22, 2024 (QZ) ..... PBR 2024/2741

(51) Int. Cl.
*A01H 5/12* (2018.01)
*A01H 6/00* (2018.01)

(52) U.S. Cl.
USPC ..... Plt./373

CPC ..... *A01H 6/00* (2018.05); *A01H 5/12* (2013.01)

(58) Field of Classification Search
USPC ..... Plt./373
See application file for complete search history.

(56) References Cited

U.S. PATENT DOCUMENTS

PP34,487 P2 * 8/2022 Ammerlaan ..... Plt./373

* cited by examiner

*Primary Examiner* — Susan Mccormick Ewoldt
*Assistant Examiner* — Zachariah Allan Kay
(74) *Attorney, Agent, or Firm* — Samuel R. McCoy, Jr.

(57) ABSTRACT

A new and distinct *Aristaloe aristata* plant named 'OVROCKS16' which is characterized by a basal rosette of relatively relaxed, succulent foliage, broad lanceolate to narrow deltoid foliage with white slightly apiculate to soft mucronate apices that darken into greyed-red as the foliage matures, green foliage that is densely covered with prominent greyed-green protuberances arranged in distinct transverse rows on both the adaxial and abaxial surfaces, serrulate to dentate foliar margins and apices, and spines arranged in a distinct longitudinal row along the abaxial midrib. The new variety has shown to be uniform and stable in the resulting generations from asexual propagation.

4 Drawing Sheets

Latin name of the genus and species: The Latin name of the genus and species of the novel variety disclosed herein is *Aristaloe aristata.*

Variety denomination: The inventive variety of *Aristaloe* disclosed herein has been given the variety denomination 'OVROCKS16'.

CROSS REFERENCE TO RELATED APPLICATIONS

This application claims priority to the Community Plant Variety Rights application number 2024/2741, filed Nov. 22, 2024, which is herein incorporated by reference.

BACKGROUND OF THE INVENTION

Parentage: 'OVROCKS16' is the product of a controlled crossing between *Aristaloe aristata* 'Green Pearl' (Community Variety Rights application number 2006/0925) and *Aristaloe aristata* 'no 1' (not patented). In 2018, the inventor initiated the crossing at a commercial greenhouse in Bleiswijk, the Netherlands. The new seedling variety was noted for its relaxed spreading foliage, greyed-red mucronate tips and prominent greyed-green protuberances and was subsequently isolated for further evaluation in order to confirm the distinctness and stability of the characteristics first observed. Upon confirmation of distinctness and stability, 'OVROCKS16' was selected for commercialization in 2019.

Asexual Reproduction: Asexual reproduction of the new cultivar 'OVPEARLS15', by way of meristematic tissue culture, was first initiated in 2019 at the inventor's commercial greenhouse in Bleiswijk, the Netherlands. Through several subsequent generations, the unique features of this cultivar have proven to be stable and true to type.

SUMMARY OF THE INVENTION

The cultivar 'OVROCKS16' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS16'. These characteristics in combination distinguish 'OVROCKS16' as a new and distinct *Aristaloe* cultivar:

1. 'OVROCKS16' exhibits relaxed foliage arranged in a spreading basal rosette, with foliage tips that rotate upwards at the base of the whorl; and
2. 'OVROCKS16' exhibits broad lanceolate to narrow deltoid leaves with white slightly apiculate to soft mucronate apices that darken into greyed-red as the foliage matures; and 3. 'OVROCKS16' exhibits green foliage that is densely covered with prominent greyed-green protuberances on both the adaxial and abaxial surfaces; and
4. 'OVROCKS16' exhibits serrulate to dentate foliar margins and apices; and
5. 'OVROCKS16' exhibits protuberances which are arranged in distinct transverse rows and bearing spines in a distinct longitudinal row along the midrib.

BOTANICAL DESCRIPTION OF THE PLANT

Figure 1:
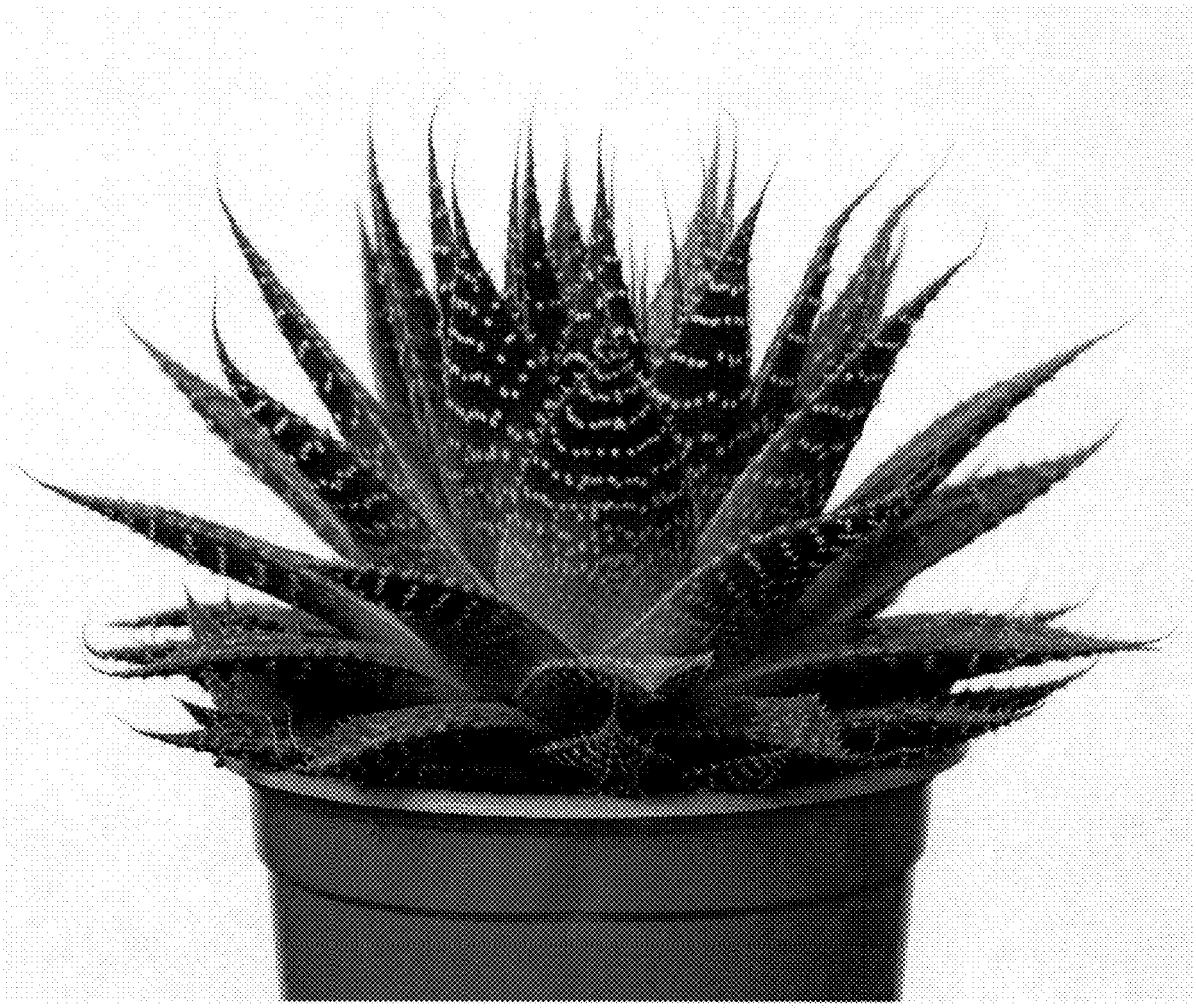
FIG. 1 illustrates, as nearly true as it is reasonably possible to make the same in color photographs of this type, an exemplary plant of 'OVROCKS16' grown in a commercial greenhouse in Heerhugowaard, the Netherlands. This plant is approximately 12 months old, planted in a 14 cm container.
Figure 2:
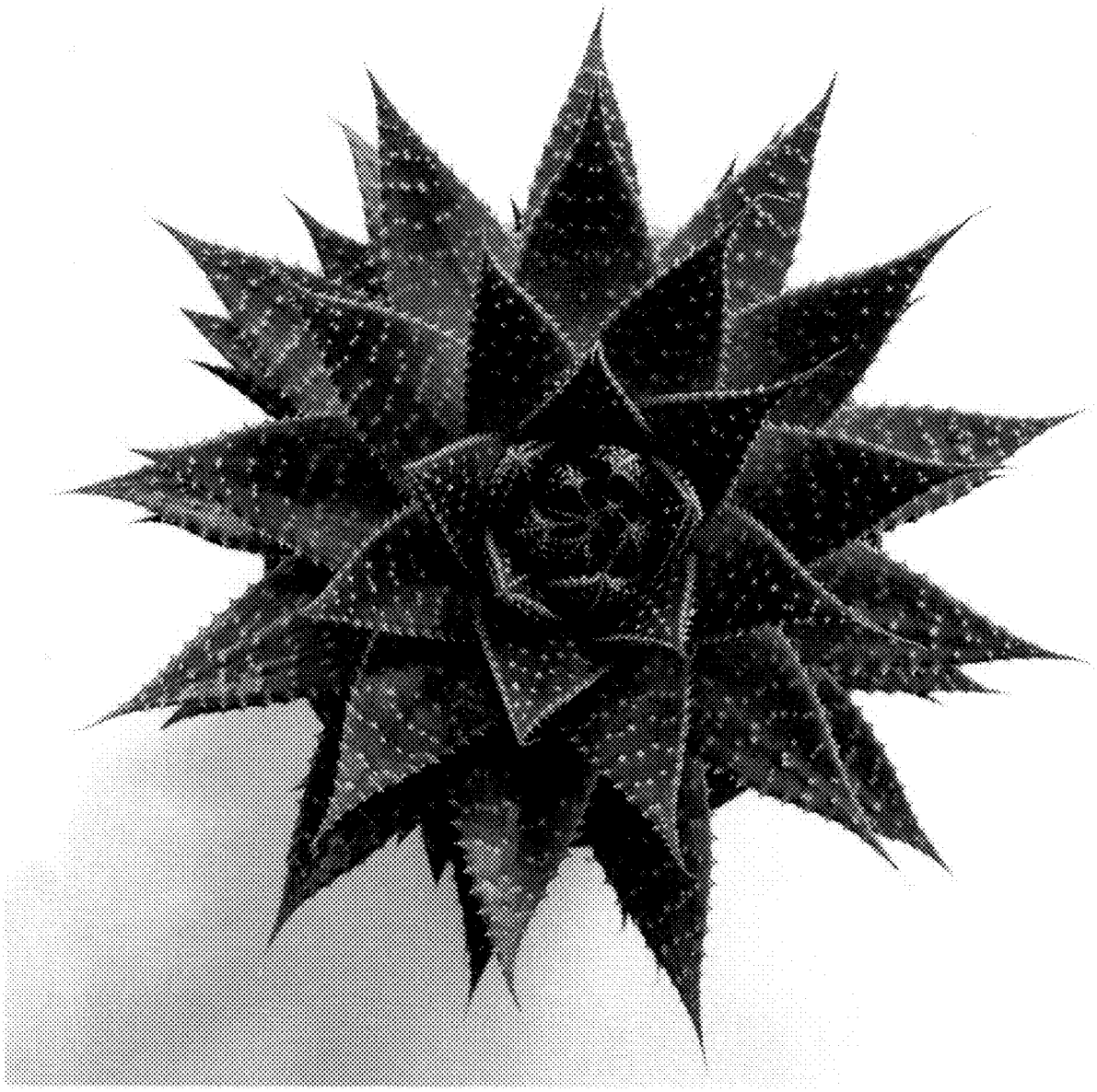
FIG. 2 illustrates, as nearly true as it is reasonably possible to make the same in color photographs of this type, the typical foliage arrangement of 'OVROCKS16'.
Figure 3:
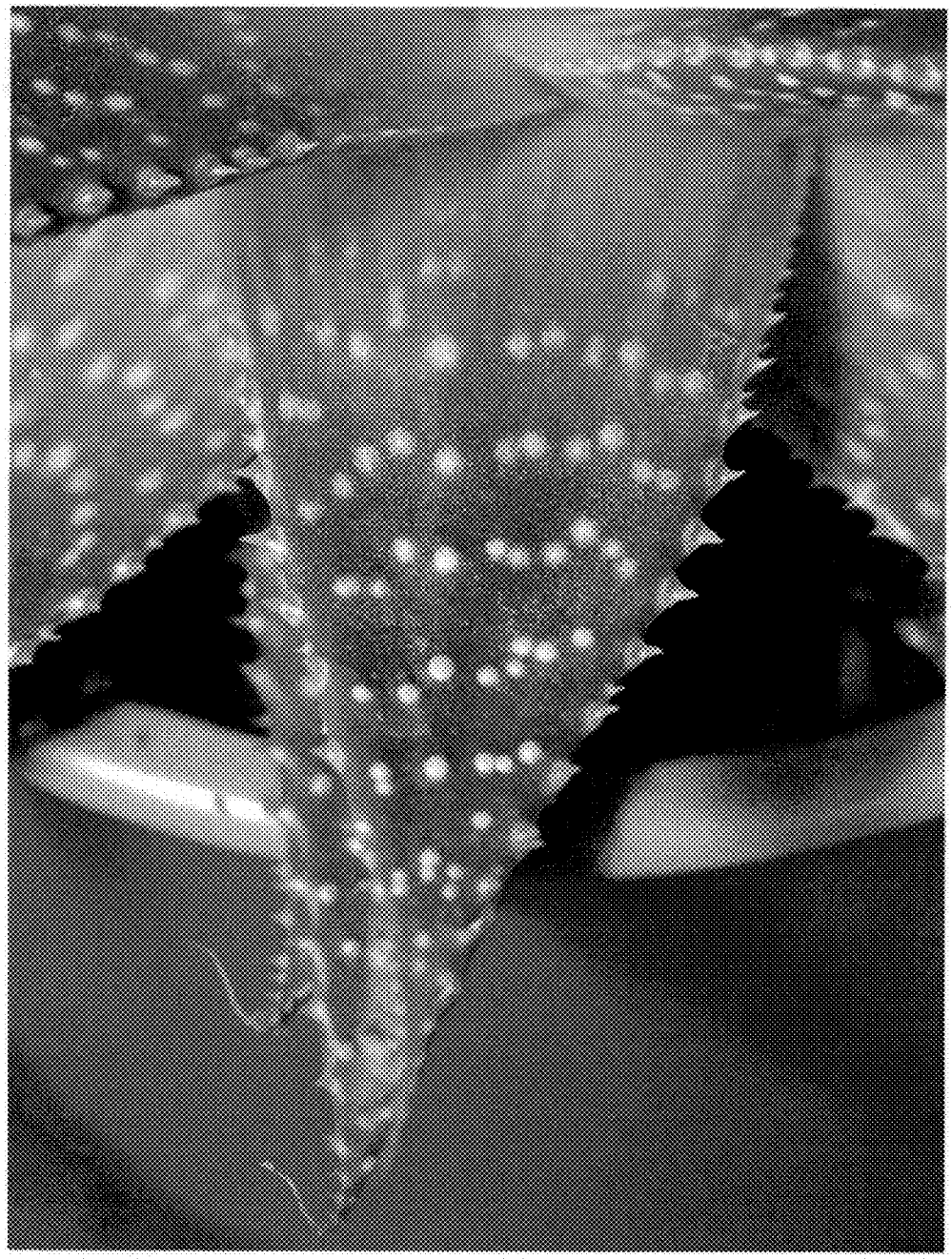
FIG. 3 illustrates, as nearly true as it is reasonably possible to make the same in color photographs of this type, the adaxial surface of the mature foliage 'OVROCKS16'.
Figure 4:
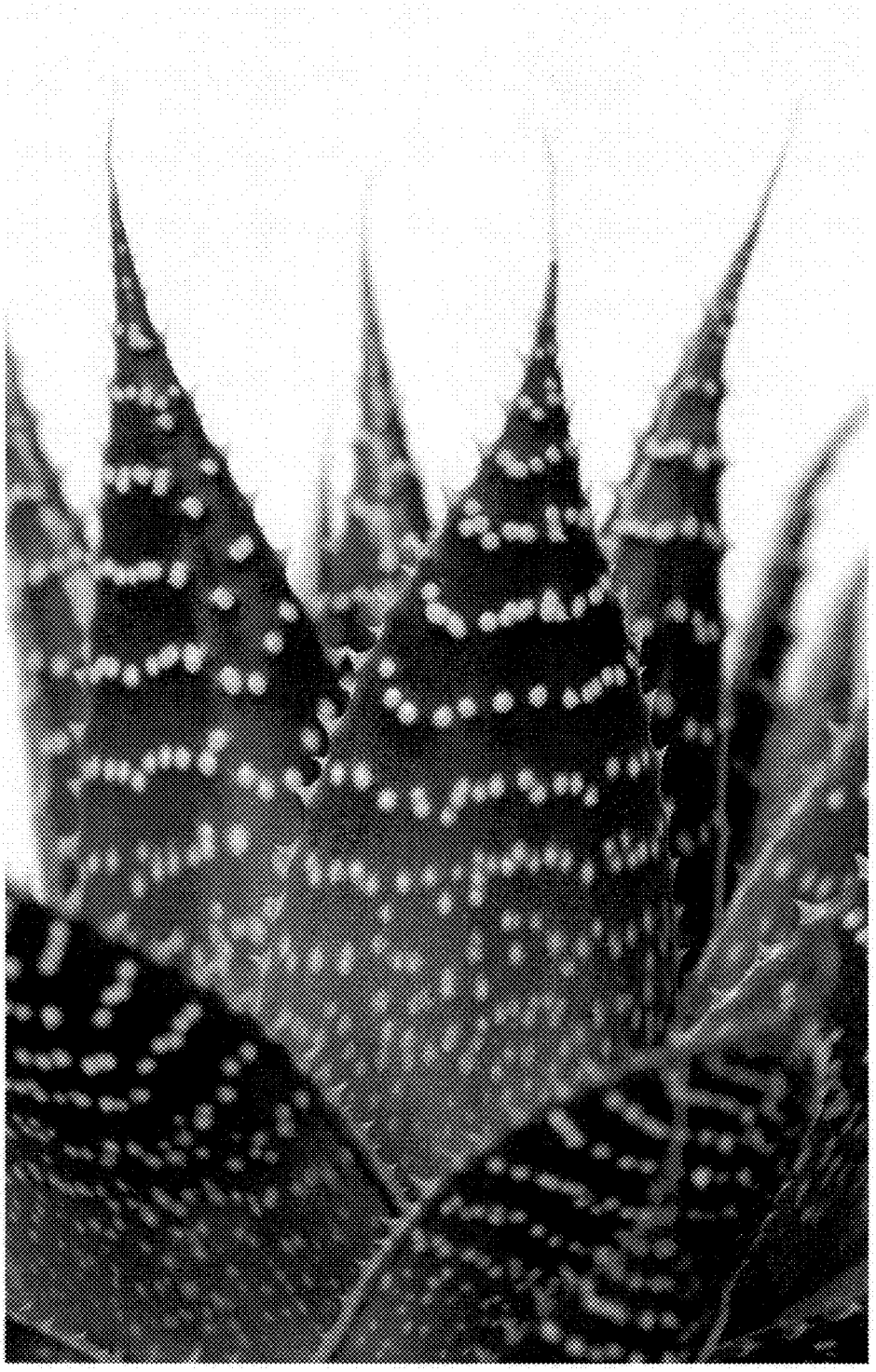
FIG. 4 illustrates, as nearly true as it is reasonably possible to make the same in color photographs of this type, the abaxial surface of the mature foliage 'OVROCKS16'.

The following observations and measurements made in November of 2024 describe averages from a sample set of six specimens of 12 months old 'OVROCKS16' plants grown in 14 cm nursery containers at commercial greenhouse in Heerhugowaard, the Netherlands. Plants were produced using conventional greenhouse production protocols for *Aristaloe* which consisted of minimal irrigation and fertilizer applications, and chemical control against common pests and diseases associated with the species as required. Plants were grown under approximately 50 percent shade and no photoperiodic treatments or artificial light was given to the plants.

Those skilled in the art will appreciate that certain characteristics will vary with older or, conversely, with younger plants. 'OVROCKS16' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVROCKS16' and a comparison with the seed parent plant, *Aristaloe aristata* 'Green Pearl' (Community Plant Variety Rights application number 2006/0925), the pollen parent plant, hybrid *Aristaloe aristata* 'no 1' (not patented, and the closest known comparator, *Aristaloe aristata* 'OVROCKS09' (U.S. Plant Pat. No. 34,487).

Plant description:

*Growth habit*.—Succulent perennial with foliage growing in a non-branched basal rosette.

*Plant shape*.—Flattened globular.

*Height from soil level to top of foliar plane*.—14.4 cm.

*Plant spread*.—Average of 22.2 cm.

*Propagation*.—Type — Leaf cuttings and meristematic tissue culture. Time to initiate rooting — Approximately 25 days at 18 degrees Celsius. Time to produce a rooted mature plant — Approximately 18 to 22 weeks grown in a 14 cm container.

*Disease and pest resistance or susceptibility*.—Neither resistance nor susceptibility to typical *Aristaloe* pests and diseases has been observed.

*Environmental tolerances*.—Adapt to, at least, USDA Zones 10 and temperatures as high as 40 degrees Celsius.

Root system:

*General*.—Fine fibrous roots.

Stems:

*Branching habit*.—Leaves in a non-branching basal rosette.

Foliage:

*Arrangement*.—Primary and secondary rosettes forming at the base; an average of 5 secondary basal rosettes form at the base of the main basal rosette.

*Division*.—Simple.

*Attachment*.—Sessile.

*Quantity*.—Approximately 63 leaves per rosette.

*Shape*.—Broad lanceolate to narrow deltoid succulent leaves.

*Dimensions*.—9.8 cm long, 3.7 cm wide, and 0.9 cm thick, on average.

*Aspect*.—Flat to very slightly concaved.

*Attitude*.—Relaxed, inner whorls are held at an average angle of 60-degrees from horizontal; lower leaves are a 20-degree angle from horizontal with leaf apices tilted upward at an average angle of 30-degrees from the lamina surface.

*Apex*.—Slightly apiculate with a soft mucronate tip.

*Base*.—Broad cuneate.

*Margin*.—Serrulate to dentate; teeth are, on average, 1.5 mm in diameter and colored greyed-green, nearest to RHS 190D, observed in distinct longitudinal rows along the margin.

*Texture, adaxial surface*.—Glabrous and moderately covered with large orbicular protuberances, each approximately 0.2 mm high and 1.5 mm in diameter; protuberances bearing spines near margins and apex.

*Texture, abaxial surface*.—Glabrous and densely covered with prominent protuberances, arranged in transverse rows; each protuberance approximately 0.2 mm high and 1.5 mm in diameter; protuberances bearing spines near margins, apex, and in a distinct longitudinal row along the midrib.

*Luster, adaxial surface*.—Slightly glossy.

*Luster, abaxial surface*.—Slightly glossy.

*Color*.—Juvenile foliage, adaxial surface — Green, nearest to RHS 137A, and fading to yellow-green towards the base, nearest to RHS 144A; the tip of the lamina is white, nearest to RHS N155D; protuberances are greyed-green, nearest to RHS 190C and 190D. Juvenile foliage, abaxial surface — Green, nearest to a blend of RHS 137B and 143A, and fading to yellow-green towards the base, nearest to a combination of RHS 143C and 144A; and white, nearest to RHS N155D, at the tip of the lamina; protuberances are colored in between greyed-green, nearest to RHS 190C and 190D. Mature foliage, adaxial surface — Green, nearest to RHS NN137A and NN137B, fading to greyed-green, nearest to RHS 194A, towards the base; the tip of the lamina appears greyed-red, nearest to RHS 182D; protuberances are greyed-green, nearest to RHS 190C and 190D. Mature foliage, abaxial surface — Green, a blend of RHS NN137A and NN137B, fading lighter towards the base to yellow-green, nearest to RHS 144A, the tip of the lamina is greyed-red, nearest to RHS 182D; protuberances are colored greyed-green, nearest to RHS 190C and 190D.

*Venation*.—No venation is visible.

*Petiole*.—No petiole; leaves are sessile.

Inflorescence: No flowering has been observed to date.

COMPARISONS WITH THE SEED PARENT PLANT

Plants of the new cultivar 'OVROCKS16' differ from the parent, 'Green Pearl' (Community Plant Variety Rights application number 2006/0925), in the following characteristics described in Table 1 below.

TABLE 1

Comparison of 'OVROCKS16' with 'Green Pearl'.

| Characteristic | 'OVROCKS16' | 'Green Pearl' |
|---|---|---|
| Foliage arrangement and attitude. | Leaves are less compact and rest closer to horizontal than 'Green Pearl'. | Leaves are more compact and grow more erect in the inner whorls 'OVROCKS16'. |
| Leaf size. | Leaves are narrower and longer than those of 'Green Pearl'. | Leaves are shorter, broader deltoid than 'OVROCKS16'. |
| General coloration of foliage. | Leaves are lighter than 'Green Pearl'; green with a yellow-green base. | Leaves are darker green than 'OVROCKS16'. |
| Leaf protuberances. | Prominent greyed-green protuberances on the mature foliage. | Less prominent than 'OVROCKS16', opaque white protuberances on mature foliage. |

COMPARISONS WITH THE POLLEN PARENT PLANT

Plants of the new cultivar 'OVROCKS16' differ from the parent, *Aristaloe aristata* 'no 1' (not patented), in the following characteristics described in Table 2 below.

TABLE 2

Comparison of 'OVROCKS16' with The Pollen Parent.

| Characteristic | 'OVROCKS16' | 'no 1' |
|---|---|---|
| General coloration of foliage. | Leaves are lighter than 'no 1'; green with a yellow-green base. | Leaves are darker green than 'OVROCKS16'. |
| Foliage arrangement and attitude. | Leaves are concave with mucronate tips that reach upward. | Leaves are more spread out than 'OVROCKS16'. |
| Leaf size. | Leaves are larger than those of the parent plant; broader and longer. | Leaves are smaller than 'OVROCKS16'. |

COMPARISONS WITH THE CLOSEST KNOWN COMPARATOR

Plants of the new cultivar 'OVROCKS16' differ from the closest known comparator, a *Aristaloe aristata* 'OVROCKS09' (U.S. Plant Pat. No. 34,487), in the following characteristics described in Table 3 below.

TABLE 3

Comparison of 'OVROCKS16' with 'OVROCKS09'

| Characteristic | 'OVROCKS16' | 'OVROCKS09' |
|---|---|---|
| Plant spread and number of leaves, on average. | 'OVROCKS16' has a larger plant spread, 22.2 cm with 63 leaves. | 'OVROCKS09' has a smaller plant spread, 12.7 cm with 70 leaves. |
| Leaf shape and size. | 'OVROCKS16' has shorter, broader lanceolate to narrow deltoid leaves compared to 'OVROCKS09'. | Longer, narrowly ovate to lanceolate leaves that are longer than 'OVROCKS13'. |
| Leaf attitude. | Erect to slightly outward facing. | Very erect to slightly inward facing. |
| General coloration of foliage. | Foliage is green fading to yellow-green at the base of the lamina. | Foliage is darker green than 'OVROCKS16'. |
| Presence of protuberances on adaxial surface of mature foliage. | Protuberances are more prominent in frequency than 'OVROCKS09'. | Protuberances are less prominent in frequency than 'OVROCKS16'. |

That which is claimed is:

1. A new and distinct variety of *Aristaloe aristata* plant named 'OVROCKS16', substantially as described and illustrated herein.

* * * * *